(12) United States Patent
Andreen

(10) Patent No.: US 7,722,627 B2
(45) Date of Patent: May 25, 2010

(54) SURGICAL LIGATION INSTRUMENT

(75) Inventor: Erik Andreen, Göteborg (SE)

(73) Assignee: Astra Tech AB, Moldal (SE)

( * ) Notice: Subject to any disclaimer, the term of this patent is extended or adjusted under 35 U.S.C. 154(b) by 458 days.

(21) Appl. No.: 10/880,534

(22) Filed: Jul. 1, 2004

(65) Prior Publication Data
US 2006/0004384 A1     Jan. 5, 2006

(51) Int. Cl.
*A61B 17/10*     (2006.01)
(52) U.S. Cl. .................................................... 606/140
(58) Field of Classification Search ......... 606/139–142, 606/153; 600/37
See application file for complete search history.

(56) References Cited

U.S. PATENT DOCUMENTS

| | | | | |
|---|---|---|---|---|
| 3,760,810 A | * | 9/1973 | Van Hoorn | 606/140 |
| 4,257,420 A | * | 3/1981 | Terayama | 606/140 |
| 4,735,194 A | * | 4/1988 | Stiegmann | 606/140 |
| 5,122,149 A | * | 6/1992 | Broome | 606/140 |
| 5,507,797 A | * | 4/1996 | Suzuki et al. | 606/140 |

FOREIGN PATENT DOCUMENTS

EP     0 310 582 A1     4/1989

* cited by examiner

*Primary Examiner*—Julian W Woo
(74) *Attorney, Agent, or Firm*—Birch, Stewart, Kolasch & Birch, LLP

(57) ABSTRACT

A surgical instrument for ligating internal tissue of a cavity in the human body by means of an elastic cord is disclosed. The instrument comprises an inner tube, having a distal and a proximal part, with the distal part having a distal end adapted to carry an elastic cord strained around it and with the proximal part arranged to be connected to a vacuum source, wherein at least one tube bend is formed between the distal and proximal part. Further, an outer discharge member is provided to push said elastic cord beyond the distal end of said tube to close around the stem of a tissue when inserted in the tube, the discharge member comprising an outer discharge part displaceably arranged around the distal part, an actuating part displaceably arranged around the proximal part, and a flexible connection part following said tube bend and arranged to transfer a movement of the actuating part to the discharge part.

20 Claims, 3 Drawing Sheets

SURGICAL LIGATION INSTRUMENT

FIELD OF THE INVENTION

The present invention relates to a surgical instrument for the ligating of internal tissues of a cavity in the human body by means of an elastic cord. The instrument comprises an inner tube, with the elastic cord strained around its front end, and a displaceable discharge-member. At displacement the elastic cord is pushed beyond the distal tube end to close around the stem of a tissue which is inserted into the distal tube end.

Further, the invention relates to a method for carrying out such a surgical ligation.

BACKGROUND OF THE INVENTION

During some years requirements for the sterilization of surgical instruments have been intensified due to increased knowledge of the risks of infection in public health and sick care. The HIV-problems contribute to the enforcement of stricter requirements for sterilization, especially of instruments for rectal use.

Surgical instruments which are utilized to devitalize tissues, such as internal hemorrhoids, by ligation, a so-called elastic ligature, represent one type of proctologic instrument which is affected by these stricter requirements for sterilization. Different types of instrument for ligating of internal hemorrhoids are known. Most of these instruments are meant to be used several times, that is, they are designated to be re-utilized several times with a sterilization in between.

Instruments suitable for one-time use, i.e. disposable instruments, are also known. For example, EP 0 310 582 by the same applicant discloses a disposable surgical instrument of the above-discussed type.

However, the prior art solutions are all affected by one or several of the following drawbacks and problems:

- they are relatively complicated and expensive to produce, which is especially disadvantageous for disposable instruments. Especially, the known devices have constructions which contain a large number of interacting parts, and with complicated transmission mechanism between the activating element and the discharge member;
- some known instruments necessitate interaction with a gripping instrument, which makes the operation difficult, since the operating surgeon must use both hands, one for the instrument and the other for the assisting tool; and
- some known instruments are relatively un-ergonomic and difficult to handle, thus making the surgeons job more difficult and hazardous.

There is therefore a need for a surgical instrument of the above-discussed type, having a less complicated construction, and especially for use as a disposable.

SUMMARY OF THE INVENTION

According to one aspect of the invention, there is provided a surgical instrument for ligating internal tissue of a cavity in the human body by means of an elastic cord, comprising:

an inner tube, having a distal and a proximal part, with the distal part having a distal end adapted to carry an elastic cord strained around it and with the proximal part arranged to be connected to a vacuum source, wherein at least one tube bend is found between the distal and proximal part; and an outer discharge member to push said elastic cord beyond the distal end of said tube to close around the stem of a tissue when inserted in the tube, the discharge member comprising an outer discharge part displaceably arranged around the distal part, an actuating part displaceably arranged around the proximal part, and a flexible connection part following said tube bend and arranged to transfer a movement of the actuating part to the discharge part.

In this application, "distal" and "proximal" are related to the user, whereby distal refers to a part or position farther from the user in the use situation and proximal to a part or position closer to the user in such a situation. However, it is to be noted that in the use situation, the distal part will normally be closer to the patient, or even inserted into the patient, whereas the proximal part will be farther from the patient.

The connection between the proximal part and the vacuum source should be understood to mean any type of connection. For example, the connection may be both direct or indirect, and the connection may be permanent or detachable.

According to another aspect of the invention, there is provided a surgical instrument comprising:

an inner tube, having a distal and a proximal part, wherein at least one tube bend is formed between the distal and proximal part;

an elastic cord strained around the distal end of the distal part;

a vacuum source connected to the proximal part; and an outer discharge member to push said elastic cord beyond the distal end of said tube, the discharge member comprising an outer discharge part displaceably arranged around the distal part, an actuating part displaceably arranged around the proximal part, and a flexible connection part following said tube bend and arranged to transfer a movement of the actuating part to the discharge part.

According to still another aspect of the invention, there is provided a method for ligating internal tissue of a cavity in the human body, comprising:

providing an inner tube, having a distal and a proximal part, wherein at least one tube bend is formed between the distal and proximal part;

providing an outer discharge member on said tube, the discharge member comprising an outer discharge part displaceably arranged around the distal part, an actuating part displaceably arranged around the proximal part, and a flexible connection part following said tube bend and arranged to transfer a movement of the actuating part to the discharge part;

arranging an elastic cord around a distal end of said distal part; and discharging the elastic cord to close around the stem of a tissue when inserted in the tube by moving the actuating part of the discharge member towards the distal part of the tube.

The surgical instrument could be used as a disposable. It has a simple construction and is made of a few simple parts which can be manufactured from relatively simple materials, i.e. materials providing an easy and cost-effective production and/or which are relatively inexpensive. The instrument is easy to activate and utilize and is designed to be connected to a vacuum source. The instrument is primarily intended for the ligating of internal hemorrhoids but can also be used for the devitalization of mucous membrane tissue in other cavities of the human body.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein.

DESCRIPTION OF PREFERRED EMBODIMENTS

Figure 1:
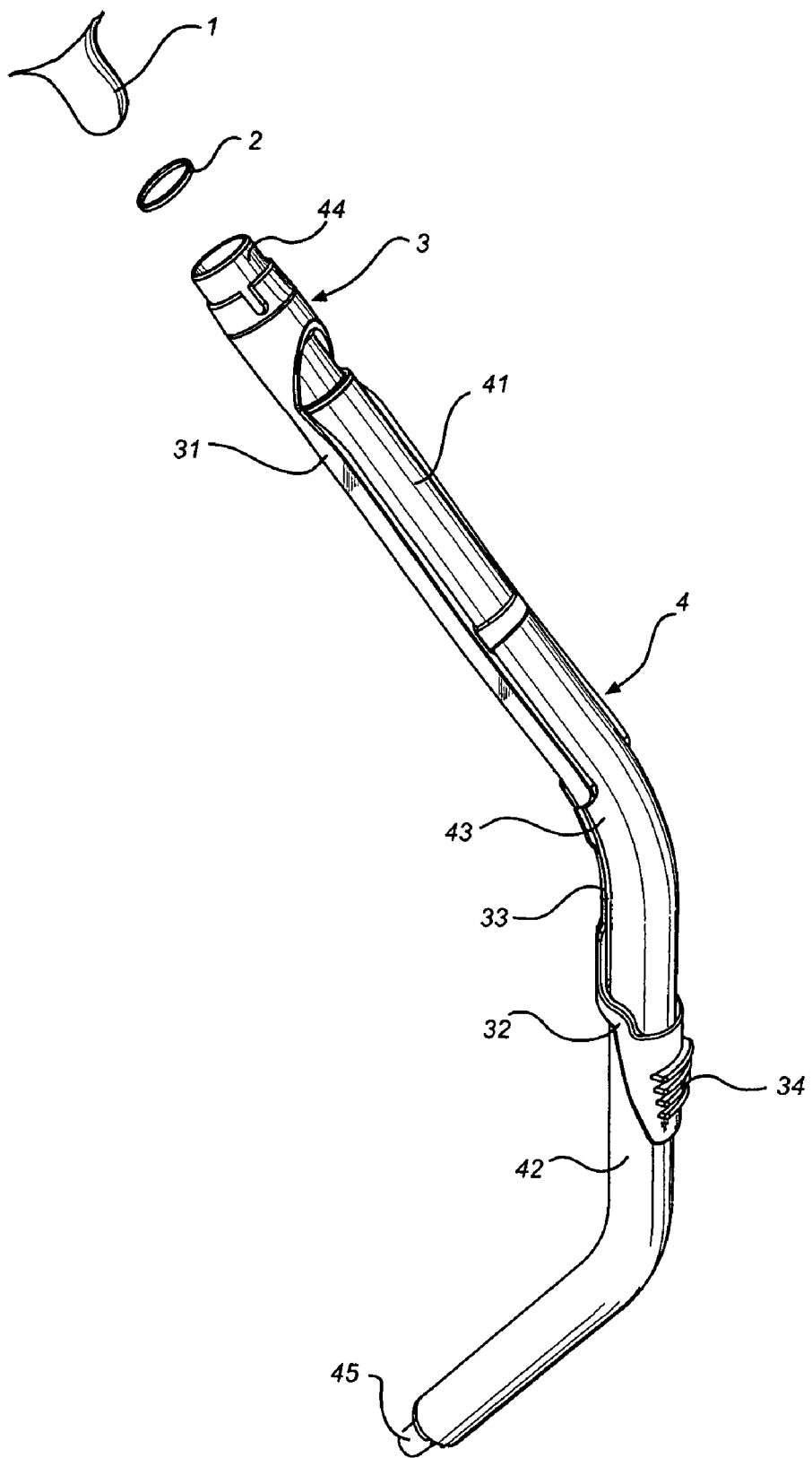
FIG. 1 is a perspective view from above, schematically illustrating a surgical instrument according to one embodiment of the invention.
Figure 2:
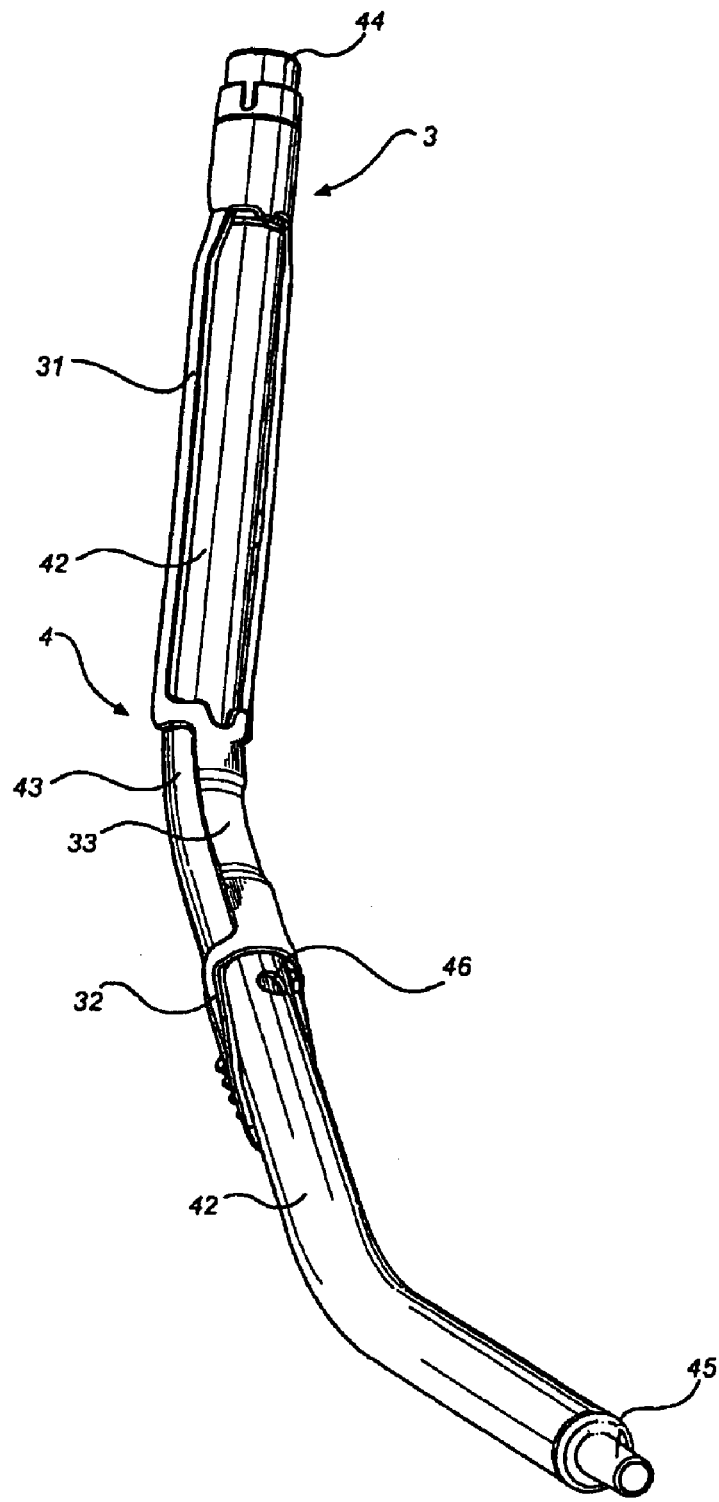
FIG. 2 is a perspective view from below of the surgical instrument of FIG. 1.

A surgical instrument for devitalization of mucous membrane tissue 1 in human body cavities, such as for the ligation of hemorrhoids, is shown in FIG. 1 and FIG. 2. The instrument comprises an angled profiled tube 4. The tube 4 has a distal part 41 and a proximal part 42, and at least one tube bend 43 is formed between the distal and proximal parts. The distal end of the distal part, i.e. the front end of the tube, is adapted to carry an elastic cord 2 strained around it. The distal part of the tube further forms a distally open receiving volume, for receiving tissue to be devitalized in it.

The proximal part 42 of the angled tube 4 is designed to be connected to a vacuum source at the rear end 45. The connection to the vacuum source could be made directly or indirectly, through other tubing. Such other tubing may be pre-connected to the rear end, and may also be integrated or otherwise permanently connected to the same. The vacuum can be created manually, for example by connecting a disposable syringe, a rubber bladder or a bellows to the tube. In such an embodiment a valve is preferably used to control the vacuum in the front cylinder. Such a control valve could be used in addition or instead of a restriction hole on the tube (see the discussion below). The syringe is preferably equipped with means for locking the plunder of the syringe in its extracted position. The bladder or bellows could for the same reason be equipped with a check valve both in inlet and outlet. Automatic vacuum sources may also be used. For example, the rear end of the tube may be connected to an electric vacuum pump, or to a general vacuum system.

The proximal part 42 preferably forms a handle part, to be held by the operating surgeon during use.

At least one restriction hole 46 is preferably provided, and situated in the underneath side of the tube, i.e. on the side forming the inner curve of the bend, in a position that is easy to reach by a finger (preferably the thumb) of the user when the hand grips the rear angled part of the tube while handling the instrument. The size of the hole is preferably defined so that it is capable of being covered by the finger. However, alternatively many types of other valve arrangements are feasible as well.

On the tube, an outer discharge-member 3 is displaceably arranged. The outer discharge member has in its initial position, a backward position in relation to the distal end of the tube, and is displaceable to push the elastic cord beyond the distal end of said tube to close around the stem of a tissue when inserted in the tube.

The discharge member comprises an outer discharge part 31 displaceably arranged around the distal part, an actuating part 32 displaceably arranged around the proximal part, and a flexible connection part 33 following the tube bend and arranged to transfer a movement of the actuating part 32 to the discharge part 31.

Figure 3:
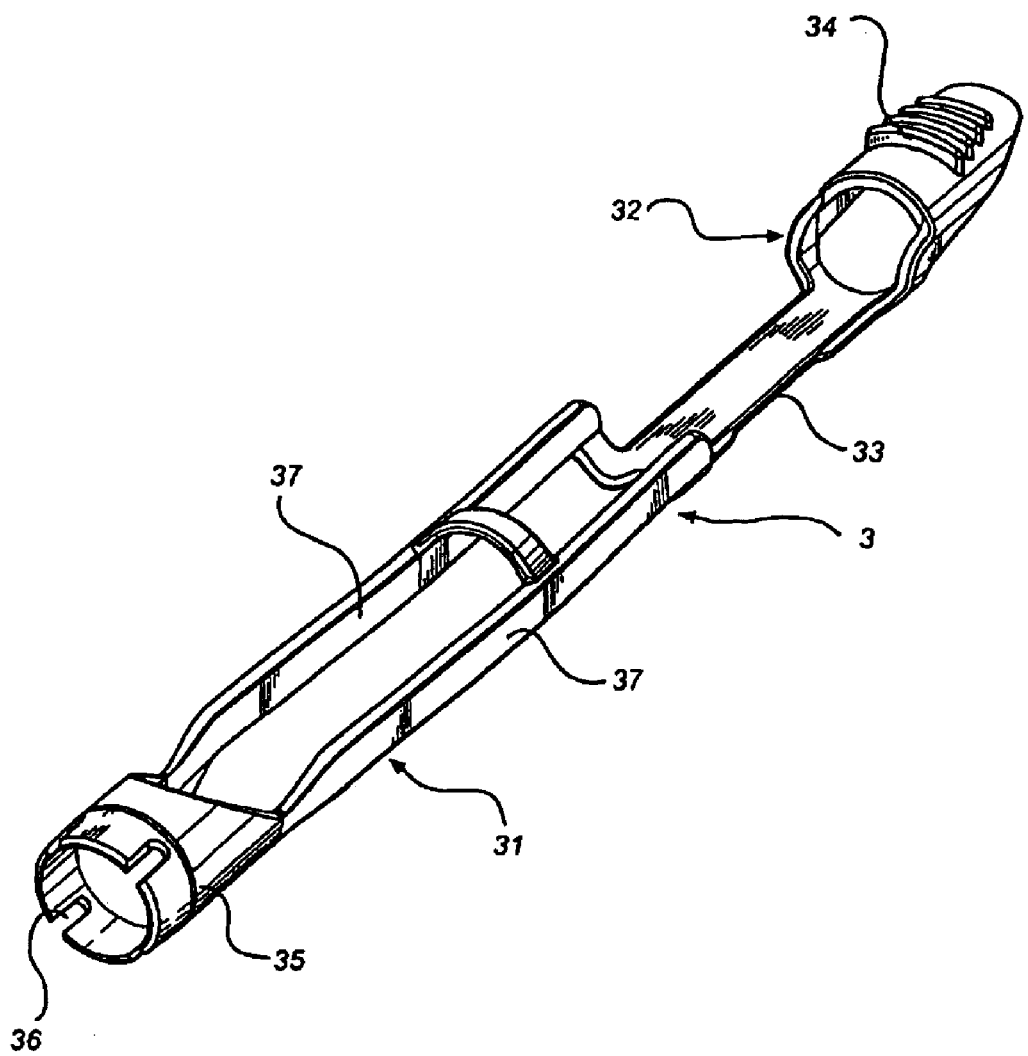
FIG. 3 is a perspective view of the discharge member of the surgical instrument in FIG. 1 and FIG. 2.

An exemplary embodiment of the discharge member is illustrated in more detail in FIG. 3. The distal part 31 preferably comprises a front discharge ring 35. The ring provides a relatively uniform force distribution towards the elastic cord to be discharged. Preferably, the abutment area of the discharge ring 35 comprises at least one, and preferably several, indentations or notches, in order to enable a smoother discharge movement for the elastic cord.

The connection between the discharge ring 35 and the flexible connection part 33 is preferably formed by two relatively rigid longitudinal strips 37, arranged on opposite sides of the tube and essentially along the axial direction of the tube. This strip construction provides a very simple and cost effective solution, and at the same time, the friction between the tube and the discharge member could be kept low, thereby enabling a very smooth and easy operation of the instrument. Possibly, one or several reinforcing and stabilizing transversal strips could be arranged between the longitudinal strips 37.

A further advantage with the above-discussed strip construction is that the strips only covers part of circumference of the tube, leaving parts of the tube uncovered. This diminishes the radial dimensions of the instrument, which improves the accessibility of the instrument. The small radial extension also provides good visibility for the surgeon performing the operation. The visibility is especially improved when the strips are arranged on the sides and/or the bottom of the tube, leaving the upper part relatively free. Hereby, the putting of the instrument in a correct position for the surgical operation, which is often made through a relatively narrow proctoscope, is greatly facilitated.

The flexible connection part 33 is preferably formed as a strip portion, having a reduced thickness making it sufficiently flexible to follow the curvature of the tube bend. The length of the flexible connection part is preferably long enough to ensure that the flexible connection part is always placed over the tube bend during operation. The flexible part is preferably arranged on the inner side of the tube bend. However, it is also feasible to arrange the flexible part on the outer side of the tube bend, or even on both said sides.

The actuating part preferably forms a displaceable ring around the tube. At least the upper side of the actuating part, i.e. the side arranged on outer curve side of the tube, is preferably provided with a gripping portion 34, in order to facilitate manual manipulation of the discharge member, in order to provide a controlled displacement of the same. The gripping portion 34 is preferably arranged and formed in order to be operated by the operators thumb when holding the instrument around the proximal part 42 of the tube.

Means could also be provided for restricting the movement of the displaceable discharge member 3 in relation to the tube 4.

The flexible connection member 33 is preferably strip shaped, making it more flexible in certain direction than in others. The strip shaped member is typically more flexible in a direction perpendicular to the width direction than in said width direction. Accordingly, such a flexible connection member, being curved to follow the bend of the tube (as illustrated in FIGS. 1 and 2), will counteract any turning or twisting of the discharge member in relation to the tube around the axial direction of the latter. Hereby, the discharge member, when arranged on the tube, is essentially only displaceable back and forth in the axial direction of the tube, i.e. in a movement following the tube length direction(s).

Further, the movement of the displaceable discharge member 3 in relation to the tube 4 in the axial direction could also be restricted. Such an axial restriction could be enabled by arranging co-operating abutment members on the outer side of the tube and the inner side of the discharge member. The abutment on at least one of the tube and the discharge member is preferably arranged around essentially the whole circumference.

In an embodiment, the tube is provided with a section with a different tube diameter, providing a forward abutment edge and backward abutment edge in the transitions to the rest of the tube. The discharge member has at least one inwardly protruding portion, which is arranged to be stopped by the forward and backward abutment edges upon displacement movement of the discharge. member. Alternatively, it is also feasible to use a movement restriction only in one axial direction, i.e. only to restrict backwards or forward movement.

The tube portion of a different diameter could be provided by arranging a separate distal tube end portion on the end of the tube, said tube end portion being insertable into the tube end, and connectable to the same.

The discharge member as disclosed above is very easy to assemble on the tube. When moved into place, the inwardly protruding member snaps into place, whereby no additional fasteners or the like are necessary. Hereby, a very fast and cost-effective assembly of the instrument becomes possible.

It is further advantageous to arrange an inner stop element (not shown) in the tube. For example, a perforated wall, an abutment edge or the like could be used. This stop element is preferably arranged relatively close to the distal end of the tube, thereby limiting the insertion volume for the tissue to be ligated. This is advantageous, since a too deep insertion of the tissue is thereby prevented.

The different parts of the disposable instrument could preferably be made of polymer material at a low cost per kilo. For example, the tube could be made of a thermoformable and extrudable material, such as polyvinyl chloride or polyamide, but many other polymer materials are feasible as well.

When operated, the instrument is connected to a vacuum source and is inserted into the cavity of the body. By covering the restriction hole 46 with a finger (e.g. the index finger), a vacuum is created in the distal end 44 of the tube, whereby a located hemorrhoid 1 can be sucked into the forward opening. By means of another finger of the hand holding the instrument (e.g. the thumb) the actuating part 34 of the discharge member 3 is subsequently pressed towards the distal part of the tube, thereby displacing the discharge member in an axial direction of the tube. The discharge end of the discharge member thereby pushes the elastic cord 2, so that it is discharged from the tube end, and is released to ligate the base of the hemorrhoid to shut off its circulation. The restriction hole 46 can now be opened to counter-balance the vacuum in the distal part of the tube and the instrument can then be removed.

The invention is in no way limited to the embodiment described above and several possible modifications of the invention are possible within the scope of the claims. One example is that the angled tube can comprise more than one bend, e.g. arranged within the distal and/or proximal part. Further, the bend may be of a large variety of different angles. Instead of the restriction hole in the tube, the vacuum in the front-cylinder can be adjusted by a valve in the vacuum hose, which may be controlled, for example, by a foot-operated control. To operate the instrument with manually operated vacuum source, a three way valve could be connected to the end of the tube and the syringe bladder or bellows is further connected to the valve. The valve is closed when the plunger of the syringe is operated to its extracted position where it is locked, or when the bladder or bellows is evacuated. The instrument is inserted into the cavity of the body with its front end close to the tissue that shall be removed. When the valve is opened a connection between the vacuum source and the distal end of the tube is opened to create a vacuum in the distal part for insertion of a tissue. The discharge member is activated for ligating the tissue. The valve can be opened to the atmospheric pressure before the instrument is withdrawn from the cavity.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims.

What is claimed is:

1. A surgical instrument for ligating internal tissue of a cavity in the human body by means of an elastic cord, comprising:
    a single wall inner tube, having a distal and a proximal part and an outermost surface, with the distal part having a distal end adapted to carry an elastic cord strained concentrically around it and with the proximal part arranged to be connected to a vacuum source, wherein at least one tube bend is formed between the distal and proximal part; and
    an outer discharge member to push said elastic cord beyond the distal end of said tube to close around the stem of a tissue when inserted in the tube, the discharge member comprising an outer discharge part displaceably arranged concentrically around a portion of the distal part, an actuating part displaceably arranged concentrically around a portion of the proximal part, and a flexible connection part following said tube bend and arranged to transfer a movement of the actuating part to the discharge part, wherein an entirety of the outer discharge member is arranged outside of the outermost surface of the single wall inner tube.

2. The surgical instrument of claim 1, wherein the flexible connecting part is arranged to follow the inner side of the tube bend.

3. The surgical instrument of claim 1, wherein the actuating part is provided with a gripping portion, said gripping portion being arranged on the side of the tube being opposite to the flexible connection part.

4. The surgical instrument of claim 3, wherein at least one restriction hole is arranged in the tube, whereby the covering and un-covering of said hole affects the vacuum at the distal part of the tube, and wherein said restriction hole is arranged close to the gripping portion but on the side of the tube being opposite to the gripping portion.

5. The surgical instrument of claim 1, wherein the proximal part is arranged to be connected to a vacuum pump or a manually operated vacuum source.

6. The surgical instrument of claim 5, wherein the manually operated vacuum source comprises a syringe, a bladders or a bellows which is connected to the proximal part of the tube via a valve.

7. The surgical instrument of claim 1, wherein at least one restriction hole is arranged in the tube, whereby the covering and un-covering of said hole affects the vacuum at the distal part of the tube.

8. The surgical instrument of claim 7, wherein the hole is arranged in such a way that vacuum in the distal part is created by the covering of the restriction hole.

9. The surgical instrument of claim 8, wherein the restriction hole is coverable by means of a finger.

10. The surgical instrument of claim 1, wherein essentially all parts of the instrument are made of polymer material to form a disposable instrument.

11. The surgical instrument of claim 1, wherein the part of the outer discharge member arranged concentrically around a portion of the distal part of the tube comprises openings leaving at least part of the tube uncovered.

12. The surgical instrument of claim 11, wherein the openings are arranged to leave at least part of the tube on the outer curve side uncovered.

13. The surgical instrument of claim 1, wherein the part of the outer discharge member arranged concentrically around a portion of the distal part of the tube comprises a discharge ring and at least one strip shaped element connecting the discharge ring and the flexible connection part.

14. The surgical instrument of claim 13, wherein the at least one strip shaped element is arranged on a side of the tube not being the outer curve side of the same.

15. A surgical instrument comprising:
    single wall inner tube, having a distal and a proximal part and an outermost surface, wherein at least one tube bend is formed between the distal and proximal part;
    an elastic cord strained concentrically around the distal end of the distal part;
    a vacuum source connected to the proximal part; and
    an outer discharge member to push said elastic cord beyond the distal end of said tube, the discharge member comprising an outer discharge part displaceably arranged concentrically around a portion of the distal part, an actuating part displaceably arranged concentrically around a portion of the proximal part, and a flexible connection part following said tube bend and arranged to transfer a movement of the actuating part to the discharge part, wherein an entirety of the outer discharge member is arranged outside of the outermost surface of the single wall inner tube.

16. A method for ligating internal tissue of a cavity in the human body, comprising:
    providing a single wall inner tube, having a distal and a proximal part and an outermost surface, wherein at least one tube bend is formed between the distal and proximal part;
    providing an outer discharge member on said tube, the discharge member comprising an outer discharge part displaceably arranged concentrically around a portion of the distal part, an actuating part displaceably arranged concentrically around a portion of the proximal part, and a flexible connection part following said tube bend and arranged to transfer a movement of the actuating part to the discharge part, wherein an entirety of the outer discharge member is arranged outside of the outermost surface of the single wall inner tube;
    arranging an elastic cord concentrically around a distal end of said distal part; and
    discharging the elastic cord to close around the stem of a tissue when inserted in the tube by moving the actuating part of the discharge member towards the distal part of the tube.

17. A surgical instrument for ligating internal tissue of a cavity in the human body by means of an elastic cord, comprising:
    an inner tube, having a distal and a proximal part and an outside surface, with the distal part having a distal end adapted to carry an elastic cord strained concentrically around it and with the proximal part arranged to be connected to a vacuum source, wherein at least one tube bend is formed between the distal and proximal part; and
    an outer discharge member to push said elastic cord beyond the distal end of said tube to close around the stem of a tissue when inserted in the tube, the discharge member comprising an outer discharge part displaceably arranged concentrically around a portion of the distal part, an actuating part displaceably arranged concentrically around a portion of the proximal part, and a flexible connection part following said tube bend and arranged to transfer a movement of the actuating part to the discharge part, wherein an entirety of the outer discharge member is arranged outside of the outside surface of the inner tube,
    wherein the actuating part extends completely around the proximal part.

18. A surgical instrument for ligating internal tissue of a cavity in the human body by means of an elastic cord, comprising:
    an inner tube, having a distal and a proximal part and an outermost surface, with the distal part having a distal end adapted to carry an elastic cord strained concentrically around it and with the proximal part arranged to be connected to a vacuum source, wherein at least one tube bend is formed between the distal and proximal part; and
    an outer discharge member to push said elastic cord beyond the distal end of said tube to close around the stem of a tissue when inserted in the tube, the discharge member comprising an outer discharge part displaceably arranged concentrically around the distal part, an actuating part displaceably arranged concentrically around the proximal part, and a flexible connection part following said tube bend and arranged to transfer a movement of the actuating part to the discharge part, wherein an entirety of the outer discharge member is arranged outside of the outermost surface of the inner tube,
    wherein the actuating part extends completely around the proximal part.

19. A surgical instrument for ligating internal tissue of a cavity in the human body by means of an elastic cord, comprising:
    an inner tube, having a distal and a proximal part and an outside surface, with the distal part having a distal end adapted to carry an elastic cord strained concentrically around it and with the proximal part arranged to be connected to a vacuum source, wherein at least one tube bend is formed between the distal and proximal part; and
    an outer discharge member to push said elastic cord beyond the distal end of said tube to close around the stem of a tissue when inserted in the tube, the discharge member comprising an outer discharge part displaceably arranged concentrically around a portion of the distal part, an actuating part displaceably arranged concentrically around a portion of the proximal part, and a flexible connection part following said tube bend and arranged to transfer a movement of the actuating part to the discharge part, wherein an entirety of the outer discharge member is arranged outside of the outside surface of the inner tube; and
    an elastic cord concentrically around a distal end of said distal part,
    wherein the actuating part extends completely around the proximal part.

20. A surgical instrument for ligating internal tissue of a cavity in the human body by means of an elastic cord, comprising:
    an inner tube of circular cross-section, having a distal and a proximal part and an outermost surface, with the distal part having a distal end adapted to carry an elastic cord strained concentrically around it and with the proximal part arranged to be connected to a vacuum source, wherein at least one tube bend is formed between the distal and proximal part; and an outer discharge member to push said elastic cord beyond the distal end of said tube to close around the stem of a tissue when inserted in the tube, the discharge member comprising an outer discharge part displaceably arranged concentrically around a portion of the distal part, an actuating part displaceably arranged concentrically around a portion of the proximal part, and a flexible connection part following said tube bend and arranged to transfer a movement of the actuating part to the discharge part, wherein an entirety of the outer discharge member is arranged outside of the outermost surface of the inner tube of circular cross-section.

* * * * *